United States Patent
Ginggen et al.

(10) Patent No.: US 8,229,562 B2
(45) Date of Patent: Jul. 24, 2012

(54) UNIVERSAL EXTERNAL CONTROL DEVICE FOR USE BY MULTIPLE CONDITIONAL ACCESS USERS WITH VARYING ACCESS TO FUNCTIONALITY OF AN IMPLANTABLE MEDICAL DEVICE

(75) Inventors: Alec Ginggen, Neuchâtel (CH); Yanik Tardy, Les Geneveys-sur-Coffrane (CH)

(73) Assignee: Codman NeuroSciences Sárl, LeLocle (SE)

( * ) Notice: Subject to any disclaimer, the term of this patent is extended or adjusted under 35 U.S.C. 154(b) by 0 days.

(21) Appl. No.: 11/586,479

(22) Filed: Oct. 25, 2006

(65) Prior Publication Data

US 2008/0103531 A1    May 1, 2008

(51) Int. Cl.
   *A61N 1/08*    (2006.01)
(52) U.S. Cl. ............... 607/31; 607/30; 607/60
(58) Field of Classification Search ........... 607/30, 607/31, 59, 60
   See application file for complete search history.

(56) References Cited

U.S. PATENT DOCUMENTS

| | | | |
|---|---|---|---|
| 3,825,898 A * | 7/1974 | Miller ..................... 340/5.28 |
| 4,373,527 A | 2/1983 | Fischell |
| 4,627,839 A | 12/1986 | Young |
| 4,731,051 A | 3/1988 | Fischell |
| 5,443,486 A | 8/1995 | Hrdlicka et al. |
| 5,772,585 A * | 6/1998 | Lavin et al. .................... 600/300 |
| 6,039,251 A | 3/2000 | Holowko et al. |
| 6,126,642 A | 10/2000 | Kriesel et al. |
| 6,269,340 B1 | 7/2001 | Ford et al. |
| 6,292,692 B1 * | 9/2001 | Skelton et al. .................... 607/5 |
| 6,579,280 B1 | 6/2003 | Kovach et al. |
| 6,796,956 B2 | 9/2004 | Hartlaub et al. |
| 6,810,290 B2 * | 10/2004 | Lebel et al. .................... 607/60 |
| 6,880,085 B1 | 4/2005 | Balczewski et al. |
| 6,961,617 B1 * | 11/2005 | Snell .............. 607/30 |
| 7,333,856 B1 * | 2/2008 | Er et al. ......... 607/30 |
| 2001/0041920 A1 | 11/2001 | Starkweather et al. |
| 2002/0151875 A1 | 10/2002 | Haller |
| 2002/0162005 A1 * | 10/2002 | Ueda et al. .................... 713/182 |
| 2002/0198513 A1 | 12/2002 | Lebel et al. |
| 2003/0065370 A1 | 4/2003 | Lebel et al. |
| 2003/0114836 A1 * | 6/2003 | Estes et al. .................. 604/890.1 |
| 2003/0204274 A1 | 10/2003 | Ullestad et al. |
| 2004/0039257 A1 * | 2/2004 | Hickle ......... 600/300 |
| 2004/0073634 A1 * | 4/2004 | Haghpassand ................ 709/220 |
| 2004/0127958 A1 * | 7/2004 | Mazar et al. .................... 607/60 |
| 2005/0108057 A1 | 5/2005 | Cohen et al. |
| 2006/0247606 A1 | 11/2006 | Batch |

* cited by examiner

*Primary Examiner* — Scott Getzow
*Assistant Examiner* — Joseph Dietrich
(74) *Attorney, Agent, or Firm* — Cheryl F. Cohen, LLC

(57) ABSTRACT

A universal external control device for use by multiple conditional access users with varying access to functionality of an implantable medical device in wireless communication therewith. Circuitry associated with the external control device is used to uniquely identify each of the conditional access users via an access device such as a key or card. Access to functionality of the implantable medical device is restricted by the universal external control device based on the conditional access user identified by the access device.

1 Claim, 5 Drawing Sheets

400 — Assigning to each of the plural conditional access users functionality associated with the implantable medical device to which that user is permitted conditional access 410 — Determining functionality associated with the implantable medical device which each of the plural conditional access users has been assigned 420 — Restricting access to the functionality associated with the implantable medical device for each of the plural conditional access users based on the determined functionality to which each of the plural conditional access users is permitted conditional access

FIG. 4

UNIVERSAL EXTERNAL CONTROL DEVICE FOR USE BY MULTIPLE CONDITIONAL ACCESS USERS WITH VARYING ACCESS TO FUNCTIONALITY OF AN IMPLANTABLE MEDICAL DEVICE

BACKGROUND OF THE INVENTION

1. Field of the Invention

An external control device for wirelessly controlling an implantable medical device, and in particular, to a universal or common external control device for use by multiple conditional access users each of which has varied access to functionality of the implantable medical device.

2. Description of Related Art

When controlling an implantable medical device it is often desirable to limit or restrict access of certain functionality to specific users. For example, in the case of a device for the dispensing of fluid medication it is imperative that the patient be restricted in the volume of medication to be dispensed; otherwise, serious health risks or possible drug dependency may result.

U.S. Pat. No. 6,126,642 is directed to a patient controlled intravenous fluid dispenser for controllably dispensing fluid medicament, e.g., pain killing drugs, intravenously at a selected uniform rate. To positively regulate the patient administration of the medicament, the dose intervals at which a selected medicament can be administered, as well as the volume of the dose of the medicament to be administered, is preset only by an authorized person such as the treating physician and, once set, cannot be altered by the patient. The device setting can only be operated or adjusted by an all mechanical mechanism, i.e., by a small physical physician's key that remains in the possession and control of the treating physician or health care worker. Specifically, the patented patient controlled analgesia device has dispensing means that includes two manually rotatable control knobs 34, 37, one of which is used to control the dose volume while the other is used to adjust the dose interval. Both rotating knobs are carried by a common operating rod. Locking means are provided for preventing rotation of control knobs 34 and 37 unless and until a locking rod, which comprises a part of the locking means, is moved from a locked position to an unlocked position via a locking key inserted into the device. In the locked position the locking rod prevents rotation of the control members. However, when the locking rod is slid to its unlocked position the control knobs can be freely rotated by the treating physician to precisely preset the volume of each dose of medicament to be delivered and preset the interval between doses.

A physical locking key having all mechanical parts is possible in the patented system because the intravenous fluid dispenser and its control knobs are located externally of the patient's body. In the case of an implantable medical device controlled wireless by an external control device, an all mechanical construction such as that in the patented system would not be possible since the control knobs on the external device have no physical interaction with the parts of the implantable medical device.

In the patented intravenous fluid dispenser, access to a single level of functionality (e.g., adjustment of the control knobs) is varied between one of two states (unlocked/accessible state versus locked/prohibited state). The system is therefore designed to only distinguish or restrict access of a single set or class of functions (e.g., adjustment of the control knobs) between these two states. By default, when the locking rod is in the first locked position patient adjustment of the control knobs is prohibited. It is only when the locking key is physically inserted into the device and the locking rod is slid to its second unlocked position (unlocked/accessible state) that the controls knobs can be rotated by the treating physician. Therefore, the patented patient controlled intravenous fluid dispenser is only suitable for a single user, e.g., the physician, having conditional access. In alternative applications, apart from the patient, conditional access to particular functionality may be warranted by more than one user. For instance, it is possible that users other than the physician should be able to adjust the control knobs but also be provided access to functionality that otherwise may remain prohibited by the physician. Modification of the patented device to accommodate multiple conditional access users having access to varied, but sometimes overlapping, functionality would require a physical key for each function to mechanically prohibit or permit access to the particular activity. In the case of more than one function this would disadvantageously require each conditional access user to carry multiple keys, wherein each key has a unique physical design to mechanically unlock parts associated with a single function.

It is therefore desirable to design a universal external control device for wireless control of an implantable medical device whose functionality is conditionally accessible by multiple conditional access users, without the use of multiple keys one for each function or a mechanical locking mechanism associated with the implantable medical device.

SUMMARY OF THE INVENTION

It is an object of the present invention to develop a universal external control device for limiting or restricting control of particular functionality of the implantable medical device among multiple conditional access users without having to physically carry around multiple keys one for each function or the need for a mechanical locking mechanism associated with the implantable medical device.

Another object of the present invention is to develop a universal external control device for limiting or restricting control of particular functionality of the implantable medical device among multiple conditional access users, wherein each user is assigned to a conditional functional access level from a hierarchical framework of multiple conditional functional access levels.

Still another object of the present invention is to develop a universal external control device for limiting or restricting control of particular functionality of the implantable medical device among multiple conditional access users, wherein each user is assigned to a set of accessible functions from a non-hierarchical framework of multiple conditional accessible functions.

A universal external control device is described herein for use by multiple conditional access users with varying access to functionality of an implantable medical device in wireless communication with the external control device. Circuitry associated with the external control device is used to uniquely identify each of the conditional access users via an access device such as a key or card. Access to functionality of the implantable medical device is restricted by the universal external control device based on the conditional access user identified by the access device.

The present invention relates to a universal external control device permitting wireless conditional access to functionality of an implantable medical device by a plurality of conditional access users. The external control device includes circuitry for identifying each of the plural conditional access users, determining functionality associated with the implantable medical device which each of the plural conditional access users has been assigned and restricting access for each of the plural conditional access users to that functionality associated with the implantable medical device based on the determined functionality to which each of the plural conditional access users has been assigned.

In addition, the invention is directed to a system for wireless conditional access to functionality of an implantable medical device by a plurality of conditional access users using a universal external control device. The system includes a plurality of access devices one for identifying each of the plural conditional access users. Circuitry is utilized for determining functionality associated with the implantable medical device which each of the plural conditional access users has been assigned and restricting access for each of the plural conditional access users to that functionality associated with the implantable medical device based on the determined functionality to which each of the plural conditional access users has been assigned.

Furthermore, the present invention relates to a method for using the universal external control device as described above. Each of the plural conditional access users is assigned functionality associated with the implantable medical device to which that user is permitted conditional access. The external control device is used to determined functionality associated with the implantable medical device which each of the plural conditional access users has been assigned. Access to the functionality associated with the implantable medical device for each of the plural conditional access users is then restricted based on the determined functionality to which each of the plural conditional access users is permitted conditional access.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which:

FIG. 4 is a flow diagram of the steps taken in the operation of a universal external control device wherein conditional access to functionality of an implantable medical device varies based on the conditional access user.

DETAILED DESCRIPTION OF THE PRESENTLY PREFERRED EMBODIMENTS OF THE INVENTION

The present invention is directed to a system and method for restricting access to functionality of an implantable medical device among multiple conditional access users using a universal external control device without the need for a mechanical locking mechanism associated with the implantable medical device or a physical key for each function. Use of a single universal external control device to be used by multiple users reduces inventory and production of different external control devices, one for each user. The implantable medical device in accordance with the present invention is accessible by numerous users. Typically, a patient's access is restricted to default non-conditional functionality of the implantable medical device which all other users also have access without restriction. Therefore, the patient is classified as a non-conditional access user in that no conditions are in place to preclude access to that functionality of which the patient has access. Multiple other individuals or users are referred to as conditional access users in that each has access to functionality which is available only upon first satisfying a condition. Typically, the condition is whether that individual or user has been authorized, assigned or permitted in advance to access such functionality.

In the exemplary embodiment shown and described the implantable medical device is a drug infusion pump. The present inventive universal external control device, however, is suitable for use with other implantable medical devices such as, but not limited to, a stimulator or sensor.

Functionality associated with the drug infusion pump to be adjusted or controlled may include any one or more of the following: (i) setting dosage volume of medication to be dispensed, (ii) setting time interval between dispensing of medication, (iii) self-testing of the drug infusion pump to ensure or verify that it is operating properly, (iv) resetting of system parameters, (v) entering of stored information about the name of the medication, (vi) setting stored drug concentration, (vii) entering of stored information about the patient (e.g., name, address, age), (viii) entering of stored information about the implantation of the pump (e.g., date, name of hospital, physician), (ix) entering of stored information about the catheter connected to the pump (e.g., manufacturer, type of catheter, length of the catheter, internal volume of the catheter), and (x) setting of date and time of the pump internal clock. Depending on the type of implantable medical device being employed other functionality may be adjusted or controlled.

Figure 1A:
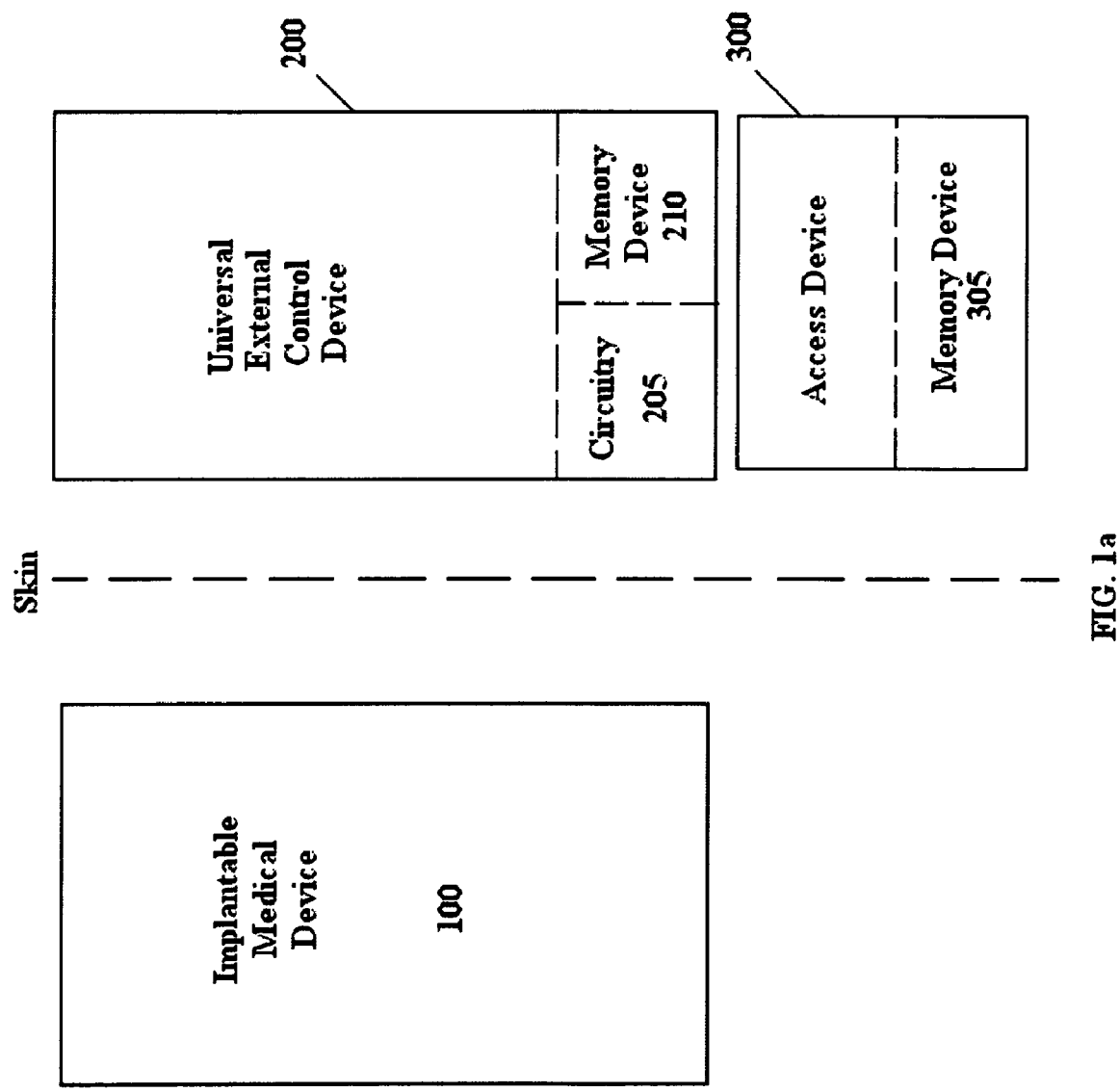
FIG. 1a is an exemplary embodiment of the universal external control device in communication with an implantable medical device in accordance with the present invention.
Figure 1B:
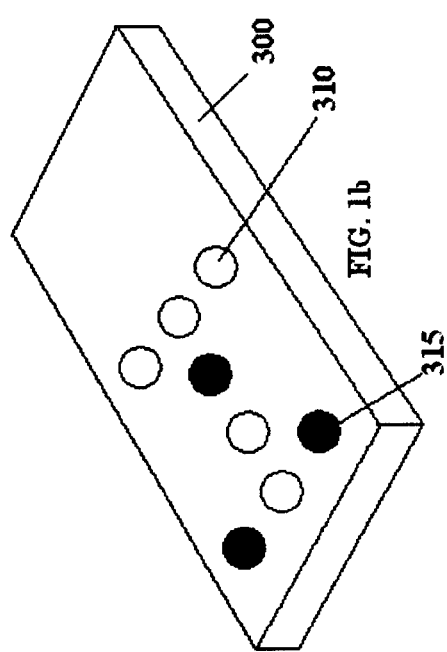
FIGS. 1b through 1e are exemplary embodiments of the access device in FIG. 1a that identifies the user based on the number of magnets and their arrangement.
Figure 1D:
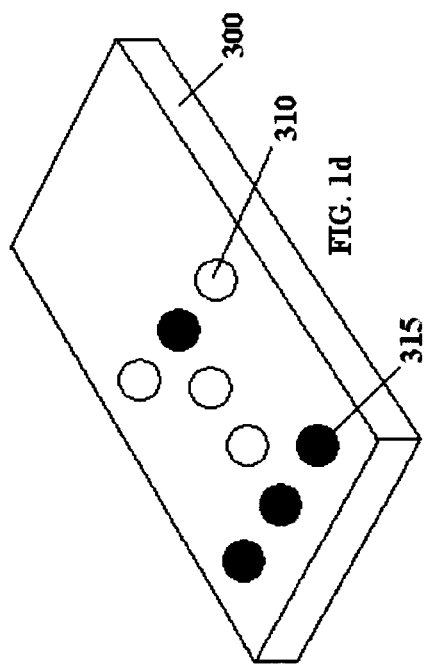
Figure 1C:
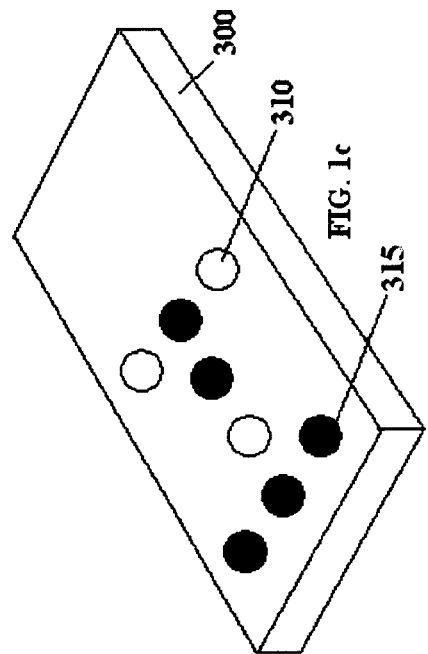
Figure 1E:
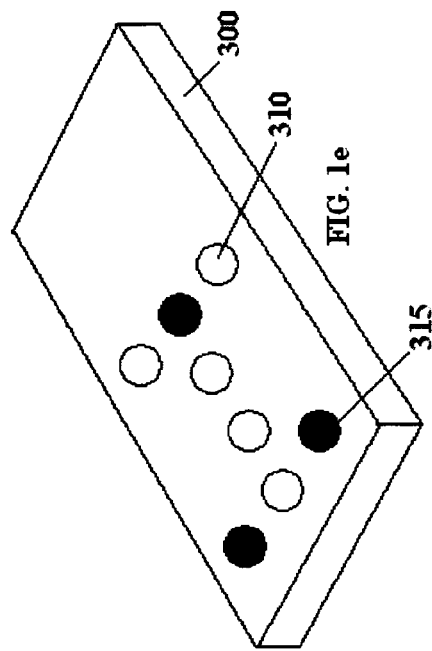

Referring to FIG. 1a, implantable drug infusion pump 100 is in wireless communication with a universal external control device 200 to be used by multiple conditional access users. Each conditional access user is provided with a single access device 300 which is a physical device for restricting or permitting access to certain functionality associated with the implantable medical device by the user in possession of the device. The inventive access device eliminates the need for any one conditional access user to carry multiple keys or cards, one associated with each function. In a first embodiment the access device 300 is a key or card inserted in a complementary size and shape slot defined in the external control device 200. The key or card 300 includes a set of magnets 315 whose number, polarity and/or position is encoded for the particular user and associated functionality to which that user is permitted or restricted access. FIGS. 1b-1e show four exemplary embodiments of the access device 300 of FIG. 1a, each having a different number of magnets and/or arrangement to uniquely identify multiple conditional access users. By way of example, FIG. 1b depicts an access device for a physician including three magnets 315 arranged in a triangular configuration. The access device provided to the technician, as shown in FIG. 1c, has five magnets 315 arranged in a "T" configuration. FIG. 1d is an access device for use in the factory during manufacture of the implantable medical device and includes four magnets 315, wherein three are arranged in a substantially linear configuration with the third displaced a predetermined distance from the other three. Lastly, FIG. 1e depicts an exemplary access device for a sales representative in which once again only three magnets 315 are employed, however, in contrast to that shown in FIG. 1b, their positioning differs. Any number of magnets and their positioning may be altered, as desired, to differentiate between multiple conditional access users. The access device 300 may be manufactured with a predetermined number of recesses 310 in a predetermined arrangement to accommodate all possible configurations. During manufacture, the appropriate number of magnets 315 complementary in shape and size need only be secured within the appropriate recesses to form the unique arrangement.

In operation the external control device 200 senses the presence/polarity of the magnets by Hall sensors disposed in the slot. To prevent improper recognition based on extraneous external magnetic fields, the external control device 200 may include a security hall sensor. The magnetic detection access device shown in FIGS. 1b-1e is advantageous in that it does not require an electrical contact between the key and external control unit that may be hampered by the presence of debris (e.g., dust) or deterioration of the contact surface. Once the particular user has been identified based on the number, placement and/or polarity of the magnets, a look-up-table (LUT) or some other storage means is used to retrieve the associated functionality to which that user is permitted or denied access.

Alternatively, access device 300 may be a smart card or other electronic identification card. External control device 200 includes circuitry 205 for reading the smart card 300 which includes circuitry and software for restricting access to the functionality of the implantable medical device 100 depending on the access accorded to the conditional access user in possession of the access device. The smart card 300 is inserted into an opening such as a slot or remotely read by complementary circuitry 205 associated with the universal external control device 200. A smart card is advantageous since it is disposable or reloadable and thus may be readily reconfigured for different users or updated without having to issue a new physical card. Stored in a memory device 305 is a unique identifier of the user and/or level of implantable medical device functionality to which the user possessing the card has access. Alternatively, the memory device 305 may store that functionality to which the user possessing the card is prohibited from accessing. In a first configuration, only a unique identification of the user is stored in the memory device 305 of the identification access device 300. When the identification access device 300 is read by complementary circuitry 205 associated with the external control device 200, based on the unique identification of the user, the associated functionality which that user is permitted or restricted access is retrieved from a look-up-table (LUT) or other storage device 210 associated with the external control device 200. As an alternative configuration, the identification access device 300 itself may store in associated memory 305 the functionality for which the user in possession of the device is permitted or restricted access. In this latter example, the unique identity of the user may, but need not necessarily, be stored in the memory of the identification access device 300. Still other mechanisms may be used to permit conditional access to privileges or functionality, for example, the user could enter a password that permits access to certain functionalities.

Two generic frameworks may be employed when defining that conditional functionality of the implantable medical device for which each conditional access user is permitted or precluded from accessing. In a first embodiment, each conditional access user is assigned a particular level from among multiple conditional functional access levels comprising a hierarchical framework. The hierarchical framework may be designed, as desired, so that a single conditional access user is assigned to each conditional functional access level, or alternatively, more than one conditional access user may be assigned to any of the conditional functional access levels. Multiple conditional functional access levels are included in a hierarchical framework comprising a lowest/first conditional functional access level and a highest/last conditional functional access level with any number of intermediate conditional functional access levels therebetween. A default non-conditional functional access level may be employed for which there is no conditional access, that is, the functionality associated with the default non-conditional functional access level is available to all users, including non-conditional access users, e.g., typically a patient. This default non-conditional functional access level may be eliminated altogether, if desired.

Starting with the lowest or first conditional functional access level each successive or higher conditional functional access level in the hierarchical framework expands or increases the user's access to functionality associated with the implantable medical device. Thus, the conditional access user assigned or associated with the lowest or first conditional functional access level has the most restricted access among the conditional access users, while the conditional access user assigned or associated with the highest or last conditional functional access level has the greatest freedom and least restriction among the conditional access users to functionality of the implantable medical device. It is also contemplated and within the intended scope of the invention to reverse the order so that the highest or last conditional functional access level has the most restricted access whereas the lowest or first conditional functional access level has the greatest access and least restriction.

By way of illustrative example, the universal external control device 200 is operable by four different users, namely, a patient, a physician, a sales representative and a technician. The patient in this exemplary embodiment is classified as a non-conditional access user having access only to default access level functionality, i.e., that functionality whose access is not restricted or prohibited among its users. Such default access level functionality may include turning off an alarm, setting of the internal clock for the pump (e.g., change of time zone or day light savings time), and interrogating the status of the pump. External control device 200 using circuitry 205 is programmed to distinguish or recognize via access device 300 among three different conditional access users, e.g., the physician, the sales representative and the technician.

Figure 2:
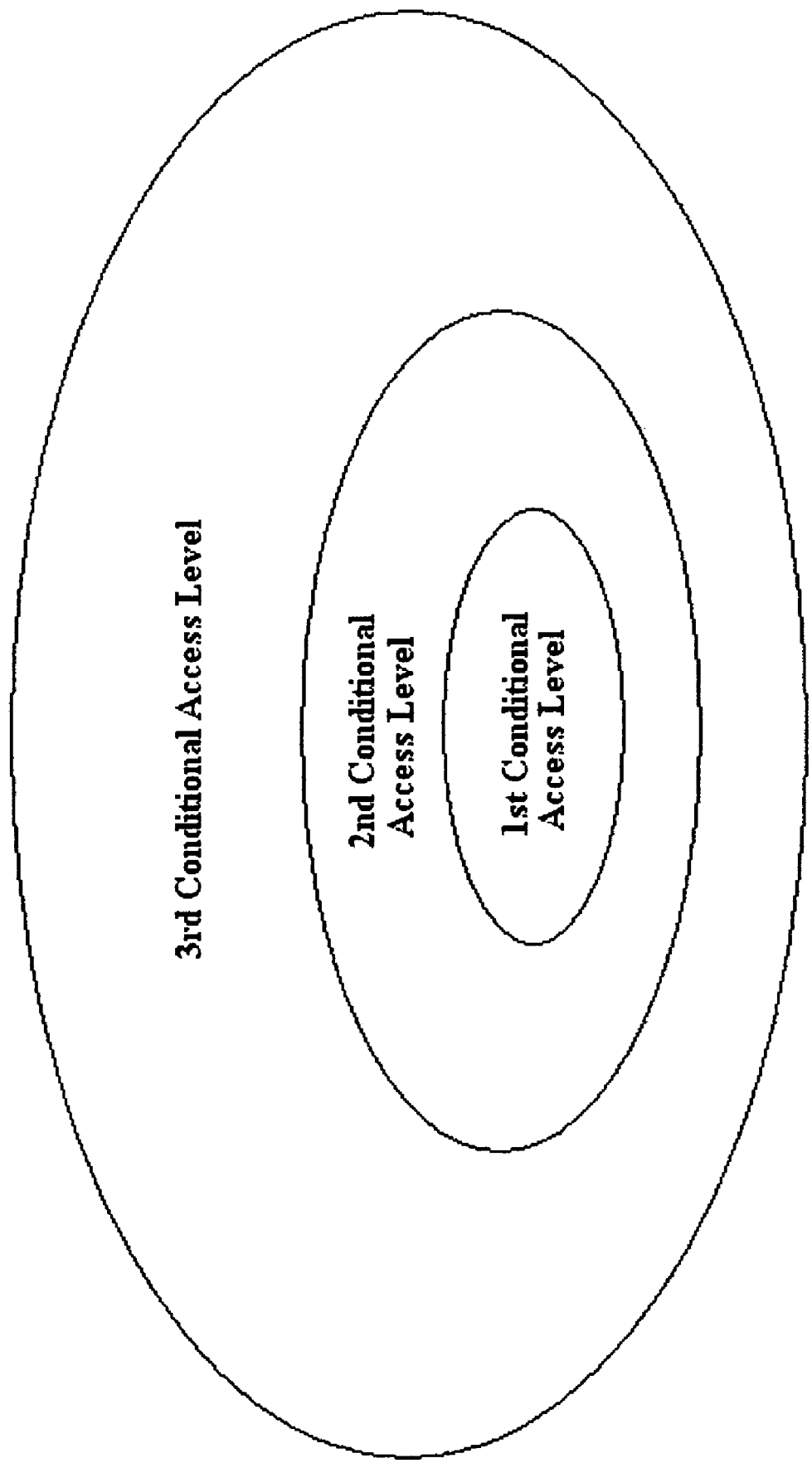
FIG. 2 is an exemplary Venn diagram depicting a hierarchical framework of three access function levels associated with three different conditional access users in accordance with the present invention.

The hierarchy of three conditional functional access levels from the first/lowest to the third/last/highest assigned to the physician, sales representative and technician, respectively, are shown in the exemplary Venn diagram of FIG. 2. That is, the physician is assigned the lowest or first conditional functional access level of the hierarchy framework that is the most restrictive of the three conditional functional access levels. At this first or lowest conditional functional access level in the hierarchical framework, the physician's access in the illustrative example is limited to adjusting the volume dosage and time interval between doses. Other functionality may be conditionally accessible by the physician such as modification of the medication parameters (e.g., type of medication, concentration of medication) or storing of information about the implantation of the pump (patient's name, age, address, date of implantation, name of hospital where implantation occurred, manufacturer of catheter, length of catheter, volume of catheter).

A next or second conditional functional access level in the hierarchical framework is assigned in the illustrative example to the sales representative. At this second conditional functional access level the sales representative is permitted access to all of the functionality associated with the first or lowest conditional functional access level. In addition, at the second conditional functional access level additional functionality such as modifying the name of the patient is available to the sales representative. Another exemplary function associated with the second conditional functional access level in the illustrative embodiment is the ability to engage in a self-testing mode to ensure or verify that the device is operating properly and then analyze the self-testing results. Any functionality associated with the second conditional functional access level and not the first or lowest conditional functional access level is therefore not available to those conditional access users assigned to the first or lowest conditional functional access level. Accordingly, the physician will be precluded from modifying the name of the patient or triggering self-testing operation.

The third or last conditional functional access level in the hierarchical framework is associated with the technician. In the exemplary embodiment, since the technician is assigned the highest or last conditional functional access level in the hierarchical framework the technician also has access to all the functionality associated with the previous levels, e.g., the first and second conditional functional access levels. It is advantageous for the technician to have full access to all functionality so that they may perform such functions as resetting the system or testing of any of the components. In summary, lower level conditional access users are prohibited from accessing any functionality associated with a higher access level than that level to which they have been assigned. With each successive higher conditional functional access level in the hierarchical framework additional functionality will be available for access by the conditional access user assigned to that particular conditional functional access level that otherwise is prohibited or restricted access by lower access level conditional access users. In a hierarchical framework conditional access users are permitted access to all functionality of conditional access levels in the framework lower than that level to which the user has been assigned.

The conditional access users in the example described above and their associated conditional functionality are not exhaustive and thus the concept of a hierarchical framework of multiple access levels may be generically described with respect to any application or situation. In general, a hierarchical framework comprises at least two conditional functional access levels including a first/lowest conditional functional access level, a highest/last conditional functional access level and may include any number of intermediate conditional functional access levels. A first conditional user's ability to control the functionality of the implantable medical device is restricted to the first/lowest conditional functional access level. This first conditional functional access level is the most restricted among all of the multiple conditional functional access levels and generically represented by the letter "a", wherein the letter "a" defines a single function or a set of more than one function of the implantable medical device. The functions associated with a second conditional functional access level are represented by "a+b", wherein "a" defines the functions associated with the first/lowest conditional functional access level, while "b" represents those functions associated with the second conditional functional access level, but not including the functions "a" associated with the first/lowest conditional functional access level. The nth or last conditional functional access level in the hierarchical framework represents the least restrictive level which provides the associated conditional access user with the most freedom and is represented by "a+b+ ... n". This nth or last conditional functional access level may have no restrictions whatsoever to the functionality of the implantable medical device. In this generic description of a hierarchical framework comprising multiple access levels the letters "a", "b" ..., "n" each may represent a single function or a set of more than one function associated with the implantable medical device and implemented by the universal external control device 200.

Figure 3:
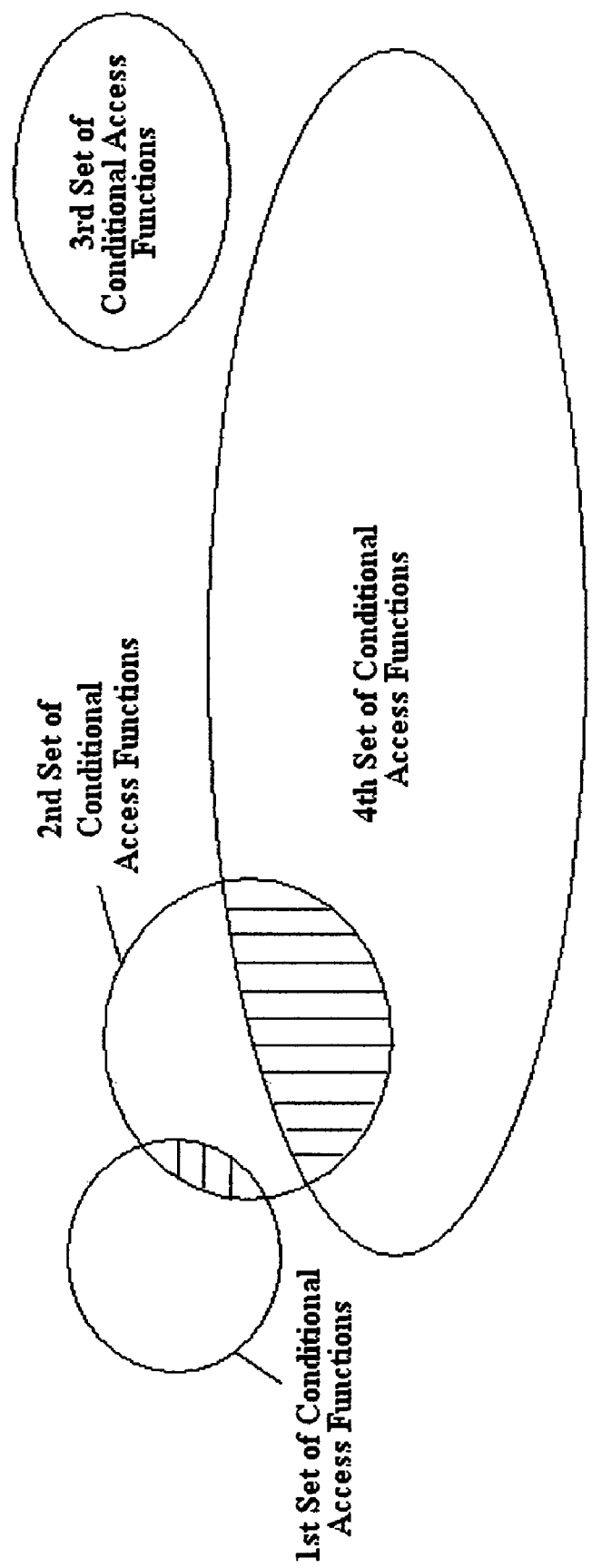
FIG. 3 is an exemplary Venn depicting a non-hierarchical framework of varied access to functionality among four conditional access users.

As an alternative to a hierarchical framework a non-hierarchical framework may be employed wherein each of the multiple conditional access users has conditional access to functionality some of which may be overlapping among multiple conditional access users and others of which may be available only to one conditional access user. By way of illustrative example, the Venn diagram in FIG. 3 of the exemplary non-hierarchical framework includes four sets of conditional access functions. In contrast to the hierarchical framework described above, there are no functional access levels employed in the non-hierarchical framework. Instead, each conditional access user is assigned to a set of one or more conditional access functions for which access by that conditional access user is permitted. For example, the physician may be permitted to access, adjust or control a first set of conditional access functions such as volume dosage and time interval between doses. A second set of conditional access functions is assigned in the illustrative example to the sales representative. Unlike the hierarchical framework described above, in the non-hierarchical framework there is only a partial overlap of functionality shared by the first and second conditional access users, as represented by the area filled in by horizontal lines. For example, the sales representative may be permitted to access volume dosage but not time interval between doses. In addition, the sales representative is permitted access to other functionality not accessible by the physician such as modifying the name of the patient or triggering a self-testing mode to ensure or verify that the device is operating properly and then analyze the self-testing results. The third set of conditional functional access level in the non-hierarchical framework is associated with the manufacturer of the implantable medical device. In the example shown in FIG. 3 the manufacturer is not permitted access to the functionality of the other conditional access users but instead has its own restricted functionality, for example, reprogramming of the implantable medical device and its associated circuitry in the case of recall for improper or malfunction in operation. The last and fourth set of conditional access functions is restricted to the technician. In this exemplary embodiment, the technician is provided with access to some of the functionality of the second set of conditional access functions (as represented by the area filled by horizontal lines) such as triggering a self-testing mode to ensure or verify that the device is operating properly but is not able to access any of the functionality of the first and third sets of conditional access functions. In summary, with the non-hierarchical framework multiple conditional access users are assigned conditional functional access independently of each other whereby there may, but need not necessarily be, any overlap or commonality of conditional functionality among the conditional access users.

In operation, if no identification access device is being read, then the external control device 200 is in default mode whereby all users including both non-conditional access users such as a patient and all conditional access users have access to that functionality that does not require satisfaction of a condition in advance. However, the flow chart depicted in FIG. 4 describes the operation of the system in the case of conditional access users. As a preliminary matter, in step 400 each of the multiple conditional access users is assigned a conditional access level or a set of conditional access functions for which conditional access is permitted by that user. Prior to gaining access to conditional functionality associated with the implantable medical device, any conditional access user is identified or recognized via the access device 300 from which the conditional access level or set of conditional functions is detected when placed in communication with the universal external control device 200, in step 410. Based on the conditional functional access set or level detected from the access device in the possession of the conditional access user access to conditional functionality associated with the implantable medical device is permitted or restricted in step 420. In the case of a hierarchical framework each conditional access level is permitted access to that functionality associated with its particular level and all lower conditional access levels. However, in the alternative case of a non-hierarchical framework each set of conditional access functions may be independent of any other or share some functionality of another set of conditional access functions.

Once again the present invention has been shown and described with respect to control by multiple conditional access users of an implantable drug infusion pump, however, the present inventive universal external control device may be employed with any other type of implantable medical device. The universal external control device permits multiple conditional access users to have restricted access to specific functionality of the implantable medical device without the need for multiple keys one for each functionality to be carried by each user.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A universal external control device for permitting wireless conditional access to functionality of an implantable medical device by a plurality of conditional access users, comprising:

circuitry for identifying each of the plural conditional access users, determining functionality associated with the implantable medical device which each of the plural conditional access users has been assigned and restricting access for each of the plural conditional access users to that functionality associated with the implantable medical device based on the determined functionality to which each of the plural conditional access users has been assigned; each of the plural conditional access users is assigned by the circuitry a particular set of conditional access functions from a non-hierarchical framework; wherein a non-conditional access user is assigned by the circuitry default non-conditional functional access to the implantable medical device which functionality does not require satisfaction of a condition in advance and is accessible by the plural conditional access users;

wherein the non-hierarchical framework includes a first set of conditional access functions and a last set of conditional access functions;

wherein the non-hierarchical framework includes at least one intermediate set of conditional access functions, and none of the conditional access functions overlap in any set of conditional access functions in the non-hierarchical network.

* * * * *